United States Patent
Crosby

(12) 
(10) Patent No.: US 6,207,445 B1
(45) Date of Patent: Mar. 27, 2001

(54) FILTRATION AND EXTRACTION DEVICE AND METHOD OF USING THE SAME

(75) Inventor: Mark A. Crosby, Boulder, CO (US)

(73) Assignee: Biostar, Inc., Boulder, CO (US)

( * ) Notice: Subject to any disclaimer, the term of this patent is extended or adjusted under 35 U.S.C. 154(b) by 0 days.

(21) Appl. No.: 09/617,394

(22) Filed: Jul. 17, 2000

Related U.S. Application Data

(62) Division of application No. 09/105,309, filed on Jun. 26, 1998, now Pat. No. 6,090,572.

(51) Int. Cl.[7] ............................. C12M 1/00; C12M 1/12; G01N 15/06
(52) U.S. Cl. ..................................... 435/283.1; 435/293.1; 435/295.3; 435/975; 422/68.1
(58) Field of Search ............................. 435/283.1, 293.1, 435/295.3, 975; 422/68.1

(56) References Cited

U.S. PATENT DOCUMENTS 6,090,572 * 7/2000 Crosby ................................. 435/29

* cited by examiner

Primary Examiner—Louise N. Leary

(57) ABSTRACT

The present invention involves a simple, disposable, manual filtration and extraction device and method of use that provides a sample directly to an analytical method. The device is capable of providing a clarified liquid ready for analysis or disposal as appropriate for the specific analyte of interest, and is capable of capturing particulate materials and allowing for further extraction of those particles directly with the device. Once extracted, the device will deliver a liquid containing the analyte of interest to an analytical method. The filtration and extraction device includes a pliant body having an open top end and an internal wall defining an inner chamber. A sealing mechanism is adapted to seal the open top end of the body. A gradient filter assembly including at least one filter is supported by a support assembly carried by the body. The pliant body is adapted to be squeezed by a user's fingers so as to impart a positive pressure in the chamber sufficient to cause a fluid in the chamber to flow through the filter assembly.

24 Claims, 2 Drawing Sheets

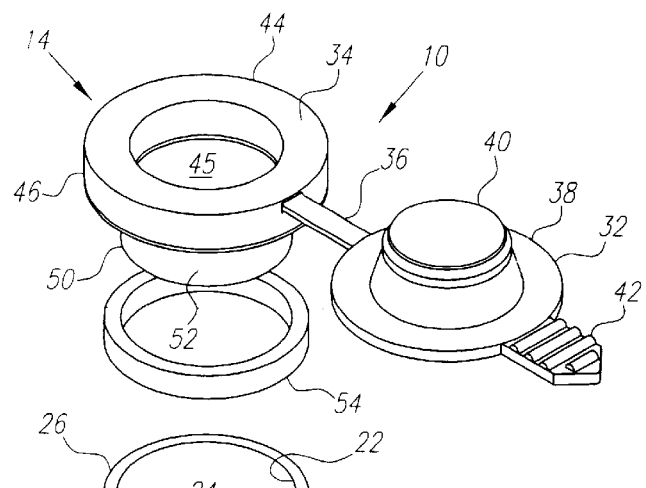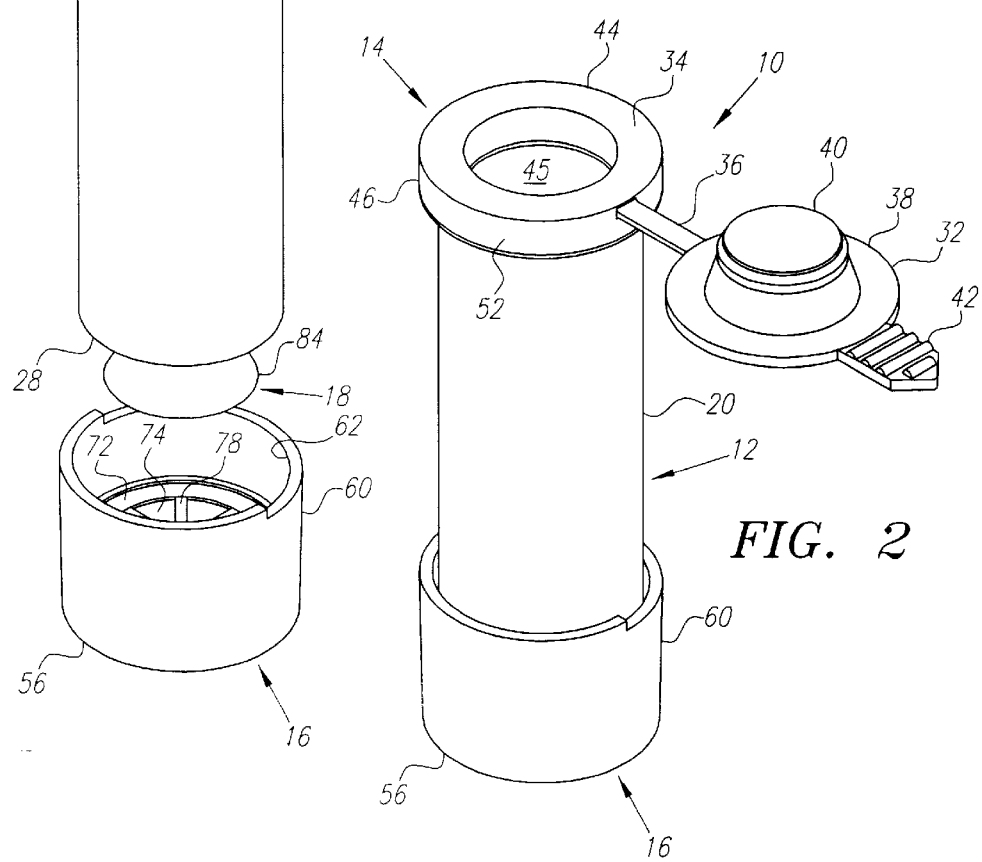

FILTRATION AND EXTRACTION DEVICE AND METHOD OF USING THE SAME

RELATED APPLICATIONS

This application is a divisional application of U.S. Ser. No. 09/105,309 by Crosby, entitled "Filtration and Extraction Device and Method of Using the Same," which was filed on Jun. 26, 1998, now U.S. Pat. No. 6,090,572 and which is incorporated herein in its entirety, including drawings.

FIELD OF THE INVENTION

The present invention relates to devices and methods for filtration of a biological fluid and/or extraction of a specific analyte from a suspended particulate.

BACKGROUND OF THE INVENTION

It is often desirable to analyze a specific component, compound, or analyte within a biological fluid such as urine. Frequently, this involves analyzing a liquid or a particulate of the biological fluid. Centrifugation is commonly used to separate a liquid solution from a particulate suspended within the liquid solution. Once separated by centrifugation the fluid is readily available for analysis. If, however, an analyte of interest is in the deposited particulate material, a more complicated process is required. The particulate material must be re-suspended and transferred from a centrifuge tube to an analysis tube. If the particulate material must be extracted prior to analysis, one or more reagents may be introduced directly into the centrifuge tube or may be introduced to the transferred, re-suspended sample in the analysis tube. If, after extraction, the analyte must be separated from other larger particulates, the sample may have to be re-centrifuged or filtered prior to analysis.

There are a number of drawbacks to the use of centrifugation. Centrifugation equipment is costly and requires a substantial amount of space. Centrifugation is a labor burden and a time burden for the operator because the centrifuge has to be loaded and unloaded. Operator error also can occur with centrifugation. Smaller, less expensive centrifugation equipment is available, but this does not eliminate the time required to process a sample, and may increase the processing time to provide adequate separation.

Plunger-like in-container pressure filtration systems have been designed to separate particles from liquid samples being tested in an effort to eliminate the necessity of centrifugation. A number of these systems involve a tube such as a test tube and a plunger mechanism that reciprocates axially within the tube. The plunger mechanism includes a filter unit at a distal end of the plunger mechanism. Downward axial movement of the filter unit via the plunger mechanism compacts particulates in the liquid sample at the bottom of the tube. Any material greater than the pore size of the filter is trapped under the filter assembly. The liquid solution can be decanted or aspirated away.

A problem with these plunger-like devices and similar devices is that they do not allow for easy recovery of the particulate material for subsequent processing. Also, the filter unit is subject to sufficient pressure during the plunging process, which can cause the filter to crack or tear. Often such devices are used with a tapered tube. Upon downward axial movement of the plunger mechanism, the diameter of the plunger mechanism and the filter unit may become the same as the inner diameter of the tapered tube. This may prevent the filter unit from being forced through the solution. If all of the liquid has not been filtered though the device, then residual liquid may contaminate the particulate material. The volume of liquid may not be easily detectable or apparent, but the contamination can be substantial. Forcing the plunger mechanism further into the tube can cause the tube to crack or break. If the plunger mechanism is not designed for removal, additional processing such as extraction of the solid within the same device may be impossible. A more complete multiple unit or multiple module device may be required that includes a removable module designed to capture the solid.

SUMMARY OF THE INVENTION

To this end, a first aspect of the present invention involves an easy to use biological fluid filtration and extraction device that provides a sample directly to an analytical method. The device is capable of providing a clarified liquid ready for analysis or disposal as appropriate for the specific analyte of interest, and is capable of capturing particulate materials and allowing for further processing, i.e., extraction, of those particles directly with the device. Once extracted, the device will deliver a liquid containing the analyte of interest to an analytical method. The device includes a pliant body having an open top end and an internal wall defining an inner chamber. A sealing mechanism is adapted to seal the open top end of the body. A gradient filter assembly including at least one filter is supported within the body by a support assembly. The pliant body is adapted to be squeezed by a user's fingers so as to impart a positive pressure in the chamber sufficient to cause a fluid in the chamber to flow through the filter assembly.

In a preferred embodiment of the filtration and extraction device, the device includes a number of features. A first feature is that the body is tubular and made of polyvinylchloride. A second feature is that the body includes a rigid ring at the top end. A third feature is that the body includes an open bottom end and the support assembly is carried by the body near the open bottom end. A fourth feature is that the sealing mechanism is a polyvinylchloride sealing cap. A fifth feature is that the support assembly includes a nozzle adapted to dispense the fluid from the device. A sixth feature is that the support assembly includes a circular, concave support that supports the filter assembly, and the support includes a plurality of radial support ribs that support the filter assembly. A seventh feature is that the support assembly includes a flat bottom surface for standing the device in an upright position on a flat surface. An eighth feature is that the support assembly is made of a rigid material. An ninth feature is that the filter assembly includes a pore size that ranges from 0.5 to 4 microns. A tenth feature is that the at least one filter is made of polysulfone, nylon, polypropylene, cellulose, or cellulose acetate. An eleventh feature is that the filter is hydrophilic. A twelfth feature is that filter assembly includes a single gradient filter and the effective pore size of the filter is in the range of 0.69 to 0.87 microns. A thirteenth feature is that the filter assembly includes multiple homogeneous filters with at least two of the filters having a different pore size, the multiple filters stacked so that a filter with a smaller pore size is located below a filter with a larger pore size, and a woven nylon membrane is located between filters. A fourteenth feature is that the periphery of the filter assembly is flush with the internal wall of the body.

A second aspect of the invention involves a filtration device including a pliant tubular body having an open end and an internal chamber, means for sealing the open end, a gradient filter assembly including at least one filter, and means for supporting the filter assembly within the tubular body, whereby the pliant tubular body is adapted to be squeezed by a user's fingers so as to impart a positive pressure in the chamber sufficient to cause a fluid in the chamber to flow through the filter assembly.

A third aspect of the invention includes a kit for filtering a biological fluid having particulate matter and liquid, and extracting an analyte from the particulate matter. The kit includes a filtration and an extraction device including a pliant tubular body having an open top end, an open bottom end, and an internal wall defining an inner chamber. The device further includes a cap assembly fixed to the body near the open top end. The cap assembly includes a cap adapted to seal the open top end. The device also includes a support assembly fixed to the body near the open bottom end, the support assembly including a circular support located within the tubular body and a nozzle adapted to dispense fluid from the device. A circular gradient filter assembly including at least one filter is fixed to the support. The pliant body is adapted to be squeezed by a user's fingers so as to impart a positive pressure in the chamber sufficient to cause a fluid in the chamber to flow through the filter assembly. The kit also includes at least one reagent for extracting the analytes from the particulate matter and a neutralization reagent for neutralizing the at least one reagent.

In a preferred embodiment of the aspect of the invention described immediately above, the at least one reagent is a protease extraction reagent and/or an alkaline detergent extraction reagent.

A fourth aspect of the invention involves a method for filtering a biological fluid having particulate matter and liquid and extracting one or more analytes from the particulate matter a device such as that described in the first aspect of the invention. The method includes adding the biological fluid to the chamber through the open top end, sealing the open top end with the sealing mechanism, squeezing the pliant body so that a positive pressure is imparted to the chamber sufficient to cause the biological fluid to flow through the filter assembly so that the particulate matter is retained by the filter assembly and the liquid is expressed from the device, unsealing the open top end of the body, adding at least one reagent to the chamber though the open top end, and squeezing the pliant body so that a positive pressure is imparted to the chamber sufficient to cause the at least one reagent to flow through the filter assembly so that the one or more analytes from the particulate matter are extracted by the at least one reagent and expressed therewith from the device for a further diagnostic assay method.

A preferred embodiment of the aspect of the invention described immediately above includes a number of features. Features one through fourteen were already identified in the first aspect of the invention described above. A fifteenth feature is that the biological fluid is urine. A sixteenth feature is that the one or more analytes is a lipopolysacharride obtained from Chlamydia and a protein from the outer cell wall of Neisseria gonorrhea. A seventeenth feature is that the particulate matter includes a virus or a bacteria that the one or more analytes is extracted from. An eighteenth feature is dispensing the at least one reagent into multiple test containers to test for different analytes. A nineteenth feature is using the expressed liquid in a diagnostic method for determining the presence of an analyte. A twentieth feature includes detecting the presence of an analyte expressed from the device using a diagnostic procedure such as radioimmunoassay, optical immunoassay, enzyme immunoassay, nucleic acid amplification, chemilluminescence, and surface plasmon resonance.

A fifth aspect of the invention involves a method for filtering a biological fluid using a device such as that described in the first aspect of the invention. The method includes adding the biological fluid to the chamber through the open top end, sealing the open top end with the sealing mechanism, and squeezing the pliant body so that a positive pressure is imparted to the chamber sufficient to cause the biological fluid to flow through the filter assembly so that particulate matter is retained by the filter assembly and a clarified liquid is expressed from the device.

A preferred embodiment of the aspect of the invention immediately described above includes a number of features. A first feature involves using the expressed liquid in a diagnostic method for determining the presence of an analyte.

A sixth aspect of the invention involves a method for filtering urine and extracting one or more lipopolysacharride analytes from one or more Chlamydia microorganisms using a device such as that described in the first aspect of the invention. The method includes adding a urine sample to the chamber through the open top end, sealing the open top end with the sealing mechanism, squeezing the pliant body so that a positive pressure is imparted to the chamber sufficient to cause the urine to flow through the filter assembly so that the one or more Chlamydia microorganisms are retained by the filter assembly and a clarified liquid is expressed from the device, unsealing the open top end of the body, adding a protease extraction reagent to the chamber though the open top end, adding an alkaline detergent extraction reagent to the chamber though the open top end, and squeezing the pliant body so that a positive pressure is imparted to the chamber sufficient to cause the reagents to flow through the filter assembly so that the one or more lipopolysacharride analytes from the one or more retained Chlamydia microorganisms are extracted by at least one of the reagents and expressed therewith from the device for a further diagnostic assay method.

In a preferred embodiment of the aspect of the invention described immediately above, the method includes detecting the presence of the one or more lipopolysacharride analytes using an optical immunoassay diagnostic procedure.

A seventh aspect of the invention involves a method for filtering urine and extracting one or more analytes from one or more Chlamydia microorganisms and/or one or more analytes from one or more Neisseria gonorrhoeae microorganisms using a device such as that described in the first aspect of the invention. The method includes adding a urine sample to the chamber through the open top end, sealing the open top end with the sealing mechanism, squeezing the pliant body so that a positive pressure is imparted to the chamber sufficient to cause the urine to flow through the filter assembly so that the one or more Chlamydia microorganisms and/or the one or more Neisseria gonorrhoeae microorganisms are retained by the filter assembly and a clarified liquid is expressed from the device, unsealing the open top end of the body, adding an alkaline detergent extraction reagent to the chamber though the open top end, and squeezing the pliant body so that a positive pressure is imparted to the chamber sufficient to cause the reagent to flow through the filter assembly so that the one or more analytes from the one or more Chlamydia microorganisms and/or the one or more analytes from the one or more Neisseria gonorrhoeae microorganisms are extracted by the extraction reagent and expressed therewith from the device into two or more extraction containers for attempting further extraction.

In a preferred embodiment of the aspect of the invention described immediately above, the method includes a number of features. A first feature is that the extraction reagents and analytes are expressed into a first extraction container and a second extraction container, and the method further includes adding a protease extraction reagent to the first extraction container for extracting one or more analytes and a neutralization reagent to the first extraction container, and adding a neutralization reagent to the second extraction container. A second feature includes detecting the presence of the one or more analytes in the respective extraction containers using respective optical immunoassay diagnostic procedures.

Other features and advantages of the inventions are set forth in the following detailed description and drawings, which are intended to illustrate, but not limit, the invention.

BRIEF DESCRIPTION OF THE DRAWINGS

FIG. 1 is an exploded perspective view of a filter and extraction device in accordance with a preferred embodiment of the invention;

FIG. 2 is a perspective view of the filter and extraction device illustrated in FIG. 1 in an assembled state.

DESCRIPTION OF THE PREFERRED EMBODIMENTS

Figure 3:
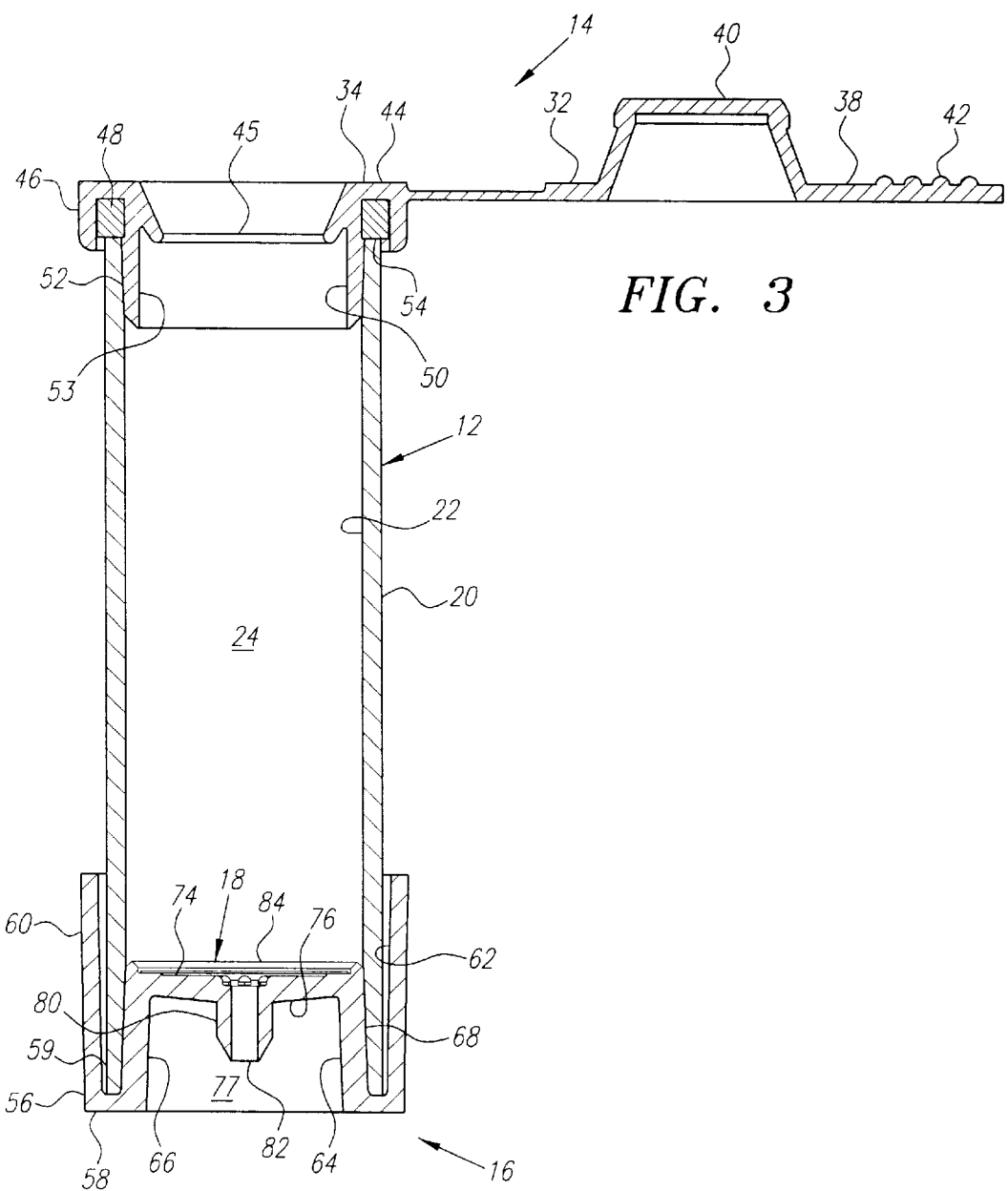
FIG. 3 is a cross-sectional view of the filter and extraction device illustrated in FIG. 1.

With reference to FIGS. 1–3, a filtration and extraction device 10 constructed in accordance with a preferred embodiment of the invention will now be described. The filtration and extraction device 10 includes a pliable tubular body 12, a cap assembly 14, a support assembly 16, and a filter assembly 18. The filtration and extraction device 10 is a simple, one-piece, manual apparatus that provides a sample directly to an analytical assay method and eliminates the aforementioned centrifugation step.

In use, a user adds a biological fluid to the tubular body 12, seals the tubular body 12 with the cap assembly 14, and squeezes the tubular body 12 with one's fingers, causing the fluid to pass through the filter assembly 18. Particulate matter in the biological fluid is retained by the filter assembly 18 for further processing, if desired, and clarified liquid is expressed from the device 10 for further processing and/or analysis if desired. If extraction of an analyte of interest from the particulate matter is desired, the device is uncapped, one or more reagents are added to the tubular body 12, the tubular body 12 is capped 14, pressure is applied to the tubular body 12, causing the one or more reagents to contact the particulate matter retained by the filter assembly 18 and the extracted analyte to be expressed from the device 10, if present.

The tubular body 12 includes an exterior wall 20 and an interior wall 22. The tubular body 12 further includes a top end 26, near where the cap assembly 14 is located, and a bottom end 28, near where the support assembly 16 is located. A main interior chamber 24 is defined by the interior wall 22, an upper part of the filter assembly 18, and a lower part of the cap assembly 14. The interior chamber 24 has a volume that is sized to allow sufficient pressure to be imported to the chamber 24 by the user's fingers so that the biological liquid flows through the filter assembly 18 without damaging the filter assembly 18. The tubular body 12 is made of a soft, pliable PVC (polyvinylchloride) tubing. However, it will be readily understood by those skilled in the art that similar materials may be used. The PVC tubing is coextruded and cut into lengths sufficient to allow the aforementioned pressure characteristics in the chamber 24.

PVC is preferably used as the material for the tubular body 12 because it is inexpensive, readily available, clear, chemically inert, biocompatible, and stable. Chemically inert means the material is stable to deformation, discoloration, cracking, splitting, etc. upon exposure to heat, biological fluid, extraction reagents, diluents or other chemical solutions. Biocompatible means the material will not bind biological materials from a solution, affect the stability, functionality, or conformation of a biological material upon contact with that material, or in anyway contaminate the biological solution with components that leach from the material in the biological solution. Stable means that the material retains all of the above characteristics for years at room temperature. The inertness and biocompatibility of the tubular body 12 allows a wide range of biological fluids to be processed in the device 10.

The cap assembly 14 includes a pliable sealing cap 32 attached to an annular support cap 34 by a hinge 36. The sealing cap 32, annular support cap 34, and hinge 36 are injection molded of a PVC material.

The sealing cap 32 includes an annular rim 38 surrounding a frustoconical sunken portion 40. A tab 42 extends from the annular rim 38.

The annular support cap 34 includes an annular rim 44 with a central aperture 45, an outer overhang 46 having an inner wall 48, and an inner overhang 50 having an outer wall 52 and an inner wall 53.

A rigid ring 54 circumferentially surrounds the top end 26 of the tubular body 12 and is chemically welded thereto. The ring 54 is injection molded of an acrylic material. The rigid acrylic ring 54 provides stiffness and support at the top end 26 of the tubular body 12, and improves sealing of the cap 34.

The annular support cap 34 resides over the top end 26 of the tubular body 12 and the ring 54. The inner wall 48 of the outer overhang 46 abuts the rigid ring 54, and the outer wall 52 of the inner overhang 50 abuts the inner wall 22 of the tubular body 12. The acrylic ring 54 is preferably chemically welded to the exterior wall 20 of the tubular body 12 by a cyclohexanone process, but similar processes may be used. No carry over of the chemical agent into the device 10 is allowed. The chemical must not alter the components of the device 10, i.e., alter the chemical inertness or biocompatibility, or cause cosmetic defects. A heat staking process may also be possible to fuse the acrylic ring 54 to the exterior 20. The outer wall 52 of the inner overhang 50 is fused to the inner wall 22 of the tubular body 12 and the inner wall 48 of the outer overhang 46 may be chemically welded to the acrylic ring 54 in the aforementioned manner.

When capped, the undersides of the frustoconical sunken portion 40 and annular rim 38 of the pliable sealing cap 32 form a sealing mechanism with the inner wall 53 of the inner overhang 50. This ensures a complete seal in the cap assembly 14 at aperture 45 and the top end 26 of the tubular body 12 so that sufficient positive pressure can be imported to the chamber 24.

In the preferred embodiment of the invention, the support assembly 16 is a single-piece assembly made of a rigid, acrylic material. The support assembly 16 includes an annular base 56 having a flat bottom surface 58 and an upper surface 59, an outer overhang 60 having an inner wall 62, and an inner overhang 64 having an inner wall 66 and an outer wall 68. The inner overhang 64 terminates at its top into a support 72. The support 72 has a concave upper surface 74 and a lower surface 76. The lower surface 76 of the support 72 and the inner wall 66 of the inner overhang 64 define an annular recess 77. The support 72 further includes a plurality of radial support ribs 78 on the concave upper surface 74 and a downwardly extending nozzle 80. The nozzle 80 terminates in the annular recess 77 and includes an outlet port 82.

The single-piece support assembly 16 is made of an acrylic material and is preferably bonded to the tubular body 12 by the aforementioned cyclohexanone process.

This bonding may occur between the outer wall 68 of the inner overhang 64 and the inner wall 22 of the tubular body 12. This bonding may also occur between the bottom end 28 of the tubular body 12 and the upper surface 59 of the annular base 56, between the outer overhang 60 and the inner overhang 64. The rigidity of the support assembly 16 gives the bottom end 28 of the tubular body 12 stability and support. The flat bottom surface 58 of the annular base 56 allows the device 10 to stand upright without user assistance on a flat support surface.

In a preferred embodiment, the filter assembly 18 includes a single circular gradient filter or membrane 84. The preferred filter 84 is sold under the name BTS-16 Memtec membrane by the US Filter Co. of San Diego, Calif. The membrane is a gradient membrane with an effective pore size of 0.69 to 0.87 microns. The membrane has sufficient tensile strength to withstand the positive pressures required for filtration and processing without tearing. A gradient filter means that the size of the pores decreases from the top of the filter 84 to the bottom of the filter 84. In other words, the pore size at the top of the filter 84 is greater than the pore size at the bottom of the filter 84. The gradient nature of the filter 84 allows for the flow of samples across the range of types, i.e., clear to turbid, while ensuring the capture of the particles of interest. A number of filter materials that are effective for this purpose include, but not by way of limitation, polysulfones such as Memtec, nylon, poypropylene, and cellulose, particularly cellulose acetate. The filter 84 should be hydrophilic or treated to be hydrophilic to reduce the non-specific capture of biologicals of interest, i.e., analytes on the filter 84 during processing. The hydrophilic nature of the filter 84 also ensures that the filter 84 wets well during processing. The suitable pore ranges for the filter is 0.5 microns to 4 microns. The type of filter 84 and pore size used depends on the particulate matter one wants to retain. The pore size can not be so small that it would clog the filter 84, but the pore size must be small enough to capture the particulate matter or organism and prevent fluid flow through the filter when no pressure is applied by the user.

Before bonding the support assembly 16 to the tubular body 12, the filter assembly 18 is sonically welded to the support 72. When the support assembly 18 is attached to the bottom 28 of the tubular body 12, the periphery of the filter assembly 18 is sealed flush with the inner wall 22 of the tubular body 12, inhibiting the collection of liquid between the periphery of the filter assembly 18 and the inner wall 22. The underside of the filter assembly 18 is supported on the radial support ribs 78, raised slight above the top of the outlet port 82. The concave upper surface 74 of the support 72 provides support to the filter 84 when the filter 84 sags due to positive pressure being imparted to the chamber 24. The support provided by the support ribs 78 and concave upper surface 74 is important for inhibiting tearing of the filter 84 under pressure.

In an alternative embodiment, the filter assembly 18 may include a stack of filters that mimic a single gradient filter. The filters each have a different, homogeneous pore size and are arranged so that a smaller pore size filter is placed below a larger pore size filter. This type of arrangement prevents clogging in the filter assembly 18, while allowing for the retention of the particulate matter of interest. To prevent vapor lock between the filters, a layer of nylon woven material sold under the name Tetko nylon (3-20/14) by Tetko, Inc. of Depew, N.Y. is inserted be restricted flow that may occur as a result of vapor lock between the filters.

In alternative embodiments, the filter assembly 18 may include a single filter having a constant pore size, a stack of filters having the same pore size, or a stack of filters generally mimicking a single gradient filter, e.g., filters stacked so that from top to bottom they generally decrease in pore size with occasional adjacent filters having the same pore size.

The filtration and extraction device 10 will now be described generally in use. A user first ensures that the sealing cap 32 is removed from the top 26 of the device 10. Next, the user adds a biological fluid to the chamber 24 through the opening 45 at the top 26 of the device 10. The opening 45 is sufficiently wide to allow a fluid to be easily added to the device 10.

As used herein, the term biological fluid is defined as a fluid containing cells, viruses, yeast, and molecules of biological origin or portions thereof, and may include urine, bladder washings, colon washings, sputum, blood, spinal fluid, tears, nasal secretions, vaginal secretions, or fluid from the respiratory, alimentary, circulatory, reproductive or other body systems.

It will readily understood by those skilled in the art that the device 10 may be applied to fluids other than biological fluids for filtering a liquid from a solid material. The device 10 may also be used for further processing of the solid material.

The tubular body 12 is sealed by generally aligning the sealing cap 32 over the top 26 of the tubular body 12 and pressing on the top of the sealing cap 32 with one's thumb so that the frustoconical sunken portion 40 of the sealing cap 32 snaps into the annular support cap 34, near the top 26 of the tubular body 12.

It should be noted, the flat bottom surface 58 of the annular base 56 allows the device 10 to be conveniently supported in an upright position on a flat support surface without user assistance. This is desirable when adding a fluid to the device 10 or in between procedural steps.

Next, the biological fluid is filtered and expressed from the device 10. This is accomplished by applying one's thumb and adjacent finger(s) on opposite sides of the exterior wall 20 of the tubular body 12 and squeezing the pliable tubular body 12. This action imparts a positive pressure in the interior chamber 24 of the tubular body 12 that is sufficient to cause the biological fluid to flow through the filter assembly 18, causing particulate material to be retained by the filter assembly 18 and resulting clarified liquid to be expressed out of the device 10 through the nozzle 80. The flow out of the device 10 is based on the biological fluid composition, the filter pore size, and the amount of pressure that can be generated by the fingers of the user when squeezing the tubular body 12. It is believed by the inventors that only a few psi are required to express the sample. Thus, the method of using the device is fairly gentle in its processing requirements. The length of the device 10 is based on allowing sufficient exposed tubular body 12 for a user's fingers to grasp the device 10 between the cap assembly 14 and the support assembly 16. If the tubular body 12 is too long then insufficient pressure is generated to express the full range of biological fluid types. The only limitation on the length and shape of the tubular body 12 is the ability to generate sufficient positive pressure in the interior chamber 24 by hand squeezing the device 10.

As used herein, the term particulate material may be any solid material which is separated from its liquid solution. Such materials may include inorganic sorbant materials such as talc and charcoal as well as glass beads. The solid material may also be organic in nature such as sepharose, microcrystalline cellulose, macro aggregated albumin and so forth. The materials may contain ligands such antibodies, antigens or haptens. Other particulate materials include, but not by way of limitation, bacteria, viruses, yeast, cells, cell fragments, large chains of nucleic acids, microorganisms, fragments of microorganisms, and large biological complexes. Microorganism is meant to include the entire microorganism or various forms or fragments the microorganism may undergo during its life cycle.

If all of the biological fluid is not removed from the interior chamber 24, the sealing cap 32 may be removed by pulling on the tab 42 with one's fingers with sufficient pressure to remove the cap 32. This allows air to enter the chamber 24. The device 10 is then re-sealed and pressure re-applied. This step can be repeated until all of the biological fluid is expressed from the chamber 24.

The method of use may end at this point if all that is desired is filtration to produce a clarified liquid for further analysis of the liquid such as through a diagnostic method for determination of the presence or amount of one or more analytes in the liquid. The device may simply be discarded in an appropriate biohazardous waste container.

However, if extraction of analytes from the particulate matter is desired for use in a further diagnostic assay method, the method of use of the device 10 also includes an extraction procedure.

As used herein, analytes may be antigens, antibodies, receptors, ligands, chelates, proteins, carbohydrates, enzymes, polysaccharides, lipopolysacharrides, nucleic acids, DNA, RNA, pesticides, herbicides, inorganic or organic compounds or any material for which a specific binding reagent may be found.

Accordingly, the next step is to remove the sealing cap 32 from the top 26 of the tubular body 12 by pulling on the 42 of the sealing cap 32 with one's fingers. One or more extraction reagents are then added to the interior chamber 24 of the tubular body 12. The type of extraction reagent(s) used depends on the analyte(s) of interest. Examples of extraction reagents that could be used, but not by way of limitation, include protease extraction reagents, alkaline detergent extraction reagents, lipase extraction reagents, acidic extraction reagents, alkaline extraction reagents, reducing extraction reagents, oxidizing extraction reagents, and organic extraction reagents. One skilled in the art would know what extraction reagent(s) to utilize to extract a desired analyte or analytes from the particulate matter. The top 26 of the device 10 is then capped, and positive pressure is imparted to the inner chamber 24 by squeezing on the exterior 20 of the pliable tubular body 12. This causes the one or more reagents to contact the particular matter retained in the filter assembly 18, breaking down the particulate material, if present, so that an analyte or analytes of interest are removed and the remaining particulate material greater than the pore size of the filter assembly 18 is left behind in the filter assembly 18. Simultaneously, the one or more reagents and analyte(s), if present, are expressed from the device 10 through the nozzle 80, into one or more extraction tubes for further extraction or diagnostic assay. The filtration and extraction device 10 is then discarded.

Examples of diagnostic assay methods include, but not by way of limitation, radio-immunoassay (RIA), enzyme immunoassay (EIA), fluorescent methods, chemiluminescence, surface plasmon resonance (SPR), optical immunoassay (OIA), spectroscopic methods, microscopic methods, and nucleic acid amplification methods. The number of extraction tubes depends on the number of analytes that are being tested for and the amount of extraction reagents used.

The filtration and extraction device 10 of the present invention is a simple, disposable, one-piece manual device that delivers a clarified biological liquid and/or one or more different analytes directly to an analytical method without the need for centrifugation. Extraction of analytes from particulate material retained in the device 10 can be accomplished in the same simple device 10, without the need to re-suspend and transfer particulate material from a centrifuge tube to an analysis tube. The device 10 also separates analytes from other larger particulates, eliminates the need to re-centrifuge or filter an analyte and particulate solution prior to analysis. Non-centrifugation manual filtering devices such as syringe-type filtering devices have been developed, but suffer from the drawbacks mentioned above in the background section of the invention.

An exemplary use of the filtration and extraction device 10 of the present invention will now be described with urine as the biological fluid and a component or elementary body of Chlamydia trachomatis (lipopolysacharride (LPS)) as the analyte to be extracted from the retained particulate matter, i.e., Chlamydia organisms. First, one milliliter of urine is removed from a collection cup and transferred to the filtration and extraction device 10. The device 10 is capped, and the urine is expressed from the device 10 into an appropriate waste container by squeezing the exterior 20 of the pliable tubular body 12. The device 10 is then opened and two drops of a protease extraction reagent sold under the trademark Chlamydia OIA Reagent 1A by BioStar, Inc. or Boulder, Colo. is added to the chamber 24. The device 10 may rest in an upright position on its flat bottom surface 58 on a bench top while the reagents are added. The Reagent 1A is followed by the addition of 6 drops of an alkaline detergent extraction reagent sold as Chlamydia Reagent 1B by the BioStar, Inc.. The device 10 is capped and the combined extraction reagents are expressed from the device 10 into an extraction tube by squeezing the exterior 20 of the pliable tubular body 12. Once all the reagent is expressed from the device 10, the device 10 may be discarded into an appropriate biohazardous waste container. Subsequently, 6 drops of neutralizer sold as Reagent 2 by BioStar, Inc. may be added to the sample in the extraction tube to neutralize the sample. By "neutralize" it is meant the addition of a buffer system which achieves a final pH range from 6.0 to 8.0. The sample in the extraction tube may then be analyzed for detection of the Chlamydia trachomatis analyte (LPS) using a test procedure such as the CHLAMYDIA OIA test procedure by BioStar, Inc.

Another exemplary use of the filtration and extraction device 10 of the present invention will now be described with urine as the biological fluid and two analytes, components of Neisseria gonorrhoeae (outer cell wall) and Chlamydia trachomatis (LPS), as the analytes to be extracted from the retained particulate matter. First, one milliliter of urine is removed from a collection cup and transferred to the filtration and extraction device 10. The device 10 is capped, and the urine is expressed from the device 10 into an appropriate waste container by squeezing the exterior 20 of the pliable tubular body 12. The device 10 is then opened and 210 microliters of alkaline detergent extraction reagent sold as Chlamydia OIA Reagent 1B by BioStar, Inc. is added to the chamber 24. The device 10 is capped and 50 microliters of extraction reagent is expressed from the device 10 into an a first extraction tube for determination of the Chlamydia trachomatis analyte (LPS) and 100 microliters of extraction reagent is expressed into a second extraction tube for determination of the Neisseria gonorrhoeae analyte (outer cell wall). Once all of the reagent is expressed from the device 10, the device 10 may be discarded into an appropriate biohazards waste container.

In the first extraction tube, 14 microliters of protease extraction reagent sold under the trademark Chlamydia OIA Reagent 1A is added to the sample, and allowed to incubate for approximately two minutes. Subsequently, 50 microliters of neutralization reagent sold as Reagent 2 by BioStar, Inc. is added to the sample, and then the resulting sample is analyzed in a Chlamydia assay, preferably optical immunoassay, for detection of the Chlamydia trachomatis analyte (LPS).

In the second extraction tube, 87 microliters of neutralization reagent sold as Reagent 2 by BioStar, Inc. is added to the sample, and then the resulting sample is analyzed in a Neisseria gonorrhoeae assay, preferably an optical immunoassay, for detection of the Neisseria gonorrhoeae analyte (outer cell wall).

The following is a table demonstrating data from the processing of 42 positive Chlamydia male urine samples. Samples were tissue culture positive based on a urethral sample. One milliliter of urine was filtered in the filtration and extraction device 10 of the present invention and one milliliter of the same urine sample was centrifuged to pellet the elementary bodies and cells in the sample. The method of filtration and extraction was the same as that described above for extraction of the Chlamydia trachomatis analyte, and the assay method was the CHLAMYDIA OIA test procedure by BioStar, Inc. The centrifuged sample was resuspended in extraction media and then processed in the CHLAMYDIA OIA test procedure. Tissue culture is considered the best means for identification of the chlamydia infection. The filtration and extraction device 10 (30/41=73.1%) performed very comparable to the conventional centrifugation method (32/42=76.2%) in the recovery of Chlamydia from a positive urine sample.

| Specimen # | Filtration and Extraction Device | Centrifugation Result |
|---|---|---|
| B1009 | + | − |
| B1024 | − | − |
| B1038 | + | + |
| B1096 | + | + |
| B1121 | + | + |
| B1176 | + | − |
| B1196 | − | − |
| B1234 | + | + |
| B0389 | + | + |
| B0431 | + | + |
| B0495 | + | + |
| B0508 | + | + |
| B0525 | − | − |
| B0529 | − | + |
| B0721 | + | + |
| B1017 | + | + |
| B1035 | + | + |
| B1058 | + | + |
| B0385 | + | + |
| B0398 | + | + |
| B0436 | − | − |
| B0509 | + | + |
| B0531 | + | + |
| B0535 | + | + |
| B0719 | − | + |
| B0742 | + | + |
| B0773 | + | + |
| B1074 | + | + |
| B1045 | − | + |
| B1002 | − | − |
| B0746 | + | + |
| B1036 | + | + |
| B0483 | + | + |
| B0748 | + | + |
| B0760 | + | + |
| B1046 | − | − |
| B0594 | + | + |
| B0570 | + | + |
| B1034 | + | + |
| B1016 | − | − |
| B0754 | + | + |
| B0710 | − | − |

Although this invention has been described in terms of a preferred embodiment, other embodiments apparent to those of ordinary skill in the art are also within the scope of this invention. Accordingly, the scope of the invention is intended to be defined only by the claims that follow.

What is claimed is:

1. A filtration and extraction device, comprising:
   a pliant body having an open top end, and an internal wall defining an inner chamber;
   a sealing mechanism adapted to seal the open top end of the body;
   a gradient filter assembly including at least one filter; and
   a support assembly carried by the body, the gradient filter assembly supported by the support assembly,
   whereby the pliant body being adapted to be squeezed by a user's fingers so as to impart a positive pressure in said chamber sufficient to cause a fluid in said chamber to flow through said filter assembly.

2. The device of claim 1, wherein the body is tubular.

3. The device of claim 2, wherein the body is made of PVC.

4. The device of claim 1, wherein the body includes a rigid ring at the top end.

5. The device of claim 1, wherein the body includes an open bottom end and the support assembly is carried by the body near the open bottom end.

6. The device of claim 1, wherein the sealing mechanism is a sealing cap.

7. The device of claim 6, wherein the sealing cap is made of PVC and is attached to the body.

8. The device of claim 1, wherein the support assembly includes a nozzle adapted to dispense said fluid from said device.

9. The device of claim 1, wherein the support assembly includes a circular, concave support that supports said filter assembly.

10. The device of claim 9, wherein the support includes a plurality of radial support ribs that support said filter assembly.

11. The device of claim 9, wherein the support assembly includes a flat bottom surface for standing the device in an upright position on a flat surface.

12. The device of claim 1, wherein the support assembly is made of a rigid material.

13. The device of claim 1, wherein the filter assembly includes a pore size that ranges from 0.5 to 4 microns.

14. The device of claim 1, wherein the at least one filter is made of a material selected from the group consisting of polysulfone, nylon, polypropylene, cellulose, and cellulose acetate.

15. The device of claim 1, wherein the filter is hydrophilic.

16. The device of claim 1, wherein filter assembly includes a single gradient filter.

17. The device of claim 16, wherein the effective pore size of the filter is in the range of 0.69 to 0.87 microns.

18. The device of claim 1, wherein the filter assembly includes multiple homogeneous filters with at least two of the filters having a different pore size, and the multiple filters stacked so that a filter with a smaller pore size is located below a filter with a larger pore size.

19. The device of claim 18, wherein a woven nylon membrane is located between filters.

20. The device of claim 1, wherein the filter assembly includes a periphery that is flush with the internal wall of the body.

21. A filtration device, comprising:

a pliant tubular body having an open end and an internal chamber;

means for sealing the open end;

a gradient filter assembly including at least one filter; and means for supporting the filter assembly within the tubular body, whereby the pliant tubular body being adapted to be squeezed by a user's fingers so as to impart a positive pressure in said chamber sufficient to cause a fluid in said chamber to flow through said filter assembly.

22. A kit for filtering a biological fluid having particulate matter and liquid, and extracting an analyte from the particulate matter, comprising:

a filtration and extraction device, comprising:

a pliant tubular body having an open top end, open bottom end, and an internal wall defining an inner chamber;

a cap assembly fixed to the body near the open top end and including a cap adapted to seal the open top end;

a support assembly fixed to the body near the open bottom end, the support assembly including a circular support located within the tubular body and an open tip adapted to dispense fluid from the device;

a circular gradient filter assembly fixed to the support, the filter assembly including at least one filter, whereby the pliant body being adapted to be squeezed by a user's fingers so as to impart a positive pressure in said chamber sufficient to cause a fluid in said chamber to flow through said filter assembly;

at least one reagent for extracting the analytes from the particulate matter; and a neutralization reagent for neutralizing the at least one reagent.

23. The device of claim 22, wherein the at least one reagent is a protease extraction reagent.

24. The device of claim 22, wherein the at least one reagent is an alkaline detergent extraction reagent.

* * * * *